United States Patent
Hsiao

(10) Patent No.: US 11,628,463 B2
(45) Date of Patent: Apr. 18, 2023

(54) ATOMIZING DIFFUSER FOR GASEOUS ENVIRONMENT CLEANING

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 238 days.

(21) Appl. No.: 17/247,252

(22) Filed: Dec. 4, 2020

(65) Prior Publication Data

US 2021/0086219 A1 Mar. 25, 2021

Related U.S. Application Data

(63) Continuation-in-part of application No. 16/259,833, filed on Jan. 28, 2019, now Pat. No. 11,154,633, which is a continuation-in-part of application No. 16/157,994, filed on Oct. 11, 2018, now Pat. No. 11,045,570, application No. 17/247,252, which is a continuation-in-part of application No. 17/102,236, filed on Nov. 23, 2020, which is a continuation-in-part of application No. 16/259,833, filed on Jan. 28, 2019, now Pat. No. 11,154,633, and a continuation-in-part of application No. 16/157,994, filed on Oct. 11, 2018, now Pat. No. 11,045,570.

(51) Int. Cl.
*B05B 17/06* (2006.01)
*B08B 3/08* (2006.01)

(52) U.S. Cl.
CPC ............ *B05B 17/0615* (2013.01); *B08B 3/08* (2013.01)

(58) Field of Classification Search
CPC .. A61L 9/14; A61L 9/122; A47K 7/00; B05B 7/0012
See application file for complete search history.

(56) References Cited

U.S. PATENT DOCUMENTS

| | | |
|---|---|---|
| 7,963,460 B2 | 6/2011 | Hsiao |
| 7,992,801 B2 | 8/2011 | Hsiao |
| 8,029,153 B2 | 10/2011 | JÖRgensen |
| 8,133,440 B2 | 2/2012 | JÖRgensen |
| 8,196,903 B2 * | 6/2012 | Jorgensen ................. A61L 9/14 261/78.2 |

(Continued)

*Primary Examiner* — Thien S Tran
(74) *Attorney, Agent, or Firm* — Sinorica LLC

(57) ABSTRACT

An atomizing diffuser for gaseous environment cleaning: includes a tank cover covered in a water tank to define an oscillation space in the tank cover so as to enhance the effect of oscillating atomized liquid, a housing shield shielding the tank cover and provided with a water filling hole for allowing direct filling of liquid in the water tank and the oscillation space, and an oscillation device with the oscillator thereof coated with a layer of acid and alkali resistant coating for oscillating the alkaline ionized water and other acid-alkaline cleaning liquids in the oscillation space into gaseous cleaning mist that is outputted to the external environmental space for sterilization, cleaning, deodorization, virus elimination, or air purification, and an umbrella-shaped panel with radial ribs provided in the housing is illuminated by light to show the beauty of a paper umbrella, matching the spray effect.

16 Claims, 8 Drawing Sheets

(56) References Cited

U.S. PATENT DOCUMENTS

| | | |
|---|---|---|
| 8,983,277 B2 | 3/2015 | Hsiao |
| 9,206,963 B2 | 12/2015 | Hsiao |
| 9,410,695 B2 | 8/2016 | Hsiao |
| 9,498,553 B2 | 11/2016 | Hsiao |
| 9,500,358 B2 | 11/2016 | Hsiao |
| 9,844,609 B2 | 12/2017 | Hsiao |
| 10,064,969 B2 | 9/2018 | Hsiao |
| 2010/0308129 A1* | 12/2010 | Jorgensen ................. A61L 9/14 239/34 |
| 2011/0051983 A1* | 3/2011 | Jorgensen ............... A61L 9/122 381/386 |
| 2011/0080724 A1* | 4/2011 | Jorgensen ................. A61L 9/14 239/338 |
| 2015/0109823 A1* | 4/2015 | Hsiao ........................ A61L 9/02 362/643 |
| 2015/0117056 A1* | 4/2015 | Hsiao ........................ A61L 9/03 362/611 |
| 2016/0195257 A1* | 7/2016 | Hsiao ................. F21V 33/0004 362/92 |

* cited by examiner

ATOMIZING DIFFUSER FOR GASEOUS ENVIRONMENT CLEANING

This application is a Continuation-in-Part of application Ser. No. 16/259,833 filed Jan. 28, 2019 and Ser. No. 17/102,236, filed Nov. 23, 2020.

BACKGROUND OF THE INVENTION

1. Field of the Invention

The present invention relates to scent releasing devices and more specifically, to an atomizing diffuser for gaseous environment cleaning, sterilization, disinfection and deodorization that generates atomization of oscillating liquid.

2. Description of the Related Art

The existing environment is cleaned, deodorized, sterilized, disinfected usually using bleach, alcohol, etc., which can cause irritation, corrosion and residue to the environment, or cause allergies or discomfort to the human body. The use of alcohol spray devices also often causes alcohol drops to remain on the table.

These liquid alcohol or bleach are not suitable for spraying in the space. Therefore, the scope of cleaning is difficult to take into account the three-dimensional space or the indoor furnishings above the ground. Some gaseous fragrance or insecticide spray devices use electrical components. When the spray device filled with corrosive liquid inside is dumped, the liquid will easily penetrate into the device and damage or affect the performance of these electrical components. The corrosive liquid overflowing the spray device is also easy to cause environmental pollution and harm to the human body, and it is not safe to use. In addition, the water tank of the spray device contains corrosive acid liquid that easily corrodes the oscillator, causing damage to the electrode layer and the problem that the formation of spray cannot produce a better environmental effect.

In the use of an existing spray device, replenishing liquid to the water tank often needs to open the outer cover of the water tank, which is inconvenient to use. However, some large spray devices use a large water tank to contain liquid, and the oscillation device on the bottom of the water tank often has a limited oscillation power. It is not efficient to oscillate a large volume of liquid at a time. There is a problem of poor atomization effect.

SUMMARY OF THE INVENTION

The present invention has been accomplished under the circumstances in view. It is therefore an object of the present invention to provide an atomizing diffuser for gaseous environment cleaning, which allows the user to directly add the liquid from the water filling hole of the housing to the water tank without opening the housing from the water tank, facilitating application.

It is another object of the present invention to provide an atomizing diffuser for gaseous environment cleaning, which combines a small volume tank cover to a large volume water tank to define an oscillation space in the tank cover, improving the efficiency of oscillating liquid atomization, and, which is so configured that when the atomizing diffuser is dumped, the liquid in the atomizing diffuser is less likely to flow into the other internal spaces or the outside environment, which helps to avoid damage to the electrical and electronic components in the atomizing diffuser and to maintain a clean and safe environment.

It is still another object of the present invention to provide an atomizing diffuser for gaseous environment cleaning, which can use alkaline ionized water, and the produced mist of alkaline ionized water is non-toxic, non-irritating, and non-residual. The produced mist of alkaline ionized water is used to clean, sterilize, deodorize, disinfect, and purify the environment space, which is safe for the environment and does not harm human health.

To achieve these and other objects of the present invention, an atomizing diffuser comprises a bottom shell, a fan, a water tank, an oscillation device, a housing, and a control unit. The bottom shell comprises a chamber defined therein, a first air inlet located in a bottom side of the chamber, and an opening formed on an upper edge of the chamber. The water tank comprises a slot, a tank bottom, a first hole, a tank cover, and an air flow channel. The slot is formed on an upper side of the water tank. The tank bottom opens the first hole. The air flow channel has one side thereof protruding in the water tank to form a protruding pipe vent, and an opposite side thereof extending out of the tank bottom to form a vent. The vent accommodates the fan. The water tank is combined in the opening of the bottom shell. The air flow channel and the fan communicate with the first air inlet in the chamber. The tank cover comprises an oscillation space, a first gap, a shield, and a first exhaust hole. The shield forms a recess shape on an inner side of the circumference of the tank cover. The recess shape of the shield has an inner side forming a shielded space. The first exhaust hole is formed on an opposite side of the tank cover. The first gap is cut on a bottom side of the tank cover. The tank cover is combined with an upper side of a bottom wall inside the water tank to simultaneously cover the first hole and the air flow channel. The shield covers the protruding pipe vent. The tank cover internally defines the oscillation space. The protruding pipe vent and the first exhaust hole communicate with the oscillation space. The oscillation device is mounted in the first hole. The oscillation device comprises an oscillator. The oscillator is externally coated with a layer of acid and alkali resistant coating. The housing comprises a cover shell. The cover shell comprises a water filling hole and an inner wall. The water filling hole is opened on an upper side of the cover shell. The inner wall protrudes downward from an inner side of the cover shell with a surrounding wall structure. The inner wall corresponds to a lower side of the water filling hole. The housing is detachably assembled to the opening of the bottom shell to shield the tank cover. The first exhaust hole of the tank cover corresponds to an inner side of the water filling hole. The inner wall has a free end thereof connected to the slot. The first exhaust hole and the oscillation space are connected to form a spray outlet path. The control unit is combined in the chamber at one side of the tank bottom and electrically connected with the oscillation device and the fan.

The acid and alkali resistant coating comprises a fluorine-containing polymer (fluoropolymer) or fluorine-containing oligomers or electronic metal coating agents commonly used in the electronics industry.

In application, the user can pour the liquid from the water filling hole into the water tank. The filled liquid flows through the first gap into the oscillation space. After connection of power supply to the control unit, the control unit drives the oscillation device to oscillate the liquid (for example, alkaline ionized water or various environmental cleaning and purification preparations, etc., or adding various natural sterilization and deodorizing agents to the liquid)

in the oscillation space, thereby generating mist. At the same time, the fan sucks in the outside air through the first air inlet. The suction air passes through the air flow channel to the shield and flows into the oscillation space without flowing out of the first exhaust hole. Therefore, the mist of alkaline ionized water (the pH value of the hydroxide ionized water electrolyzed with pure water is about 10 to 12.5) is delivered through the first exhaust hole to the external environment to sterilize, clean, deodorize, eliminate viruses or purify the air. The atomizing diffuser is safe to use and does not affect human health. This at least improves the existing problem of hand injury caused by alcohol or chemical cleaning fluids.

DETAILED DESCRIPTION OF THE PREFERRED EMBODIMENT

Figure 1:
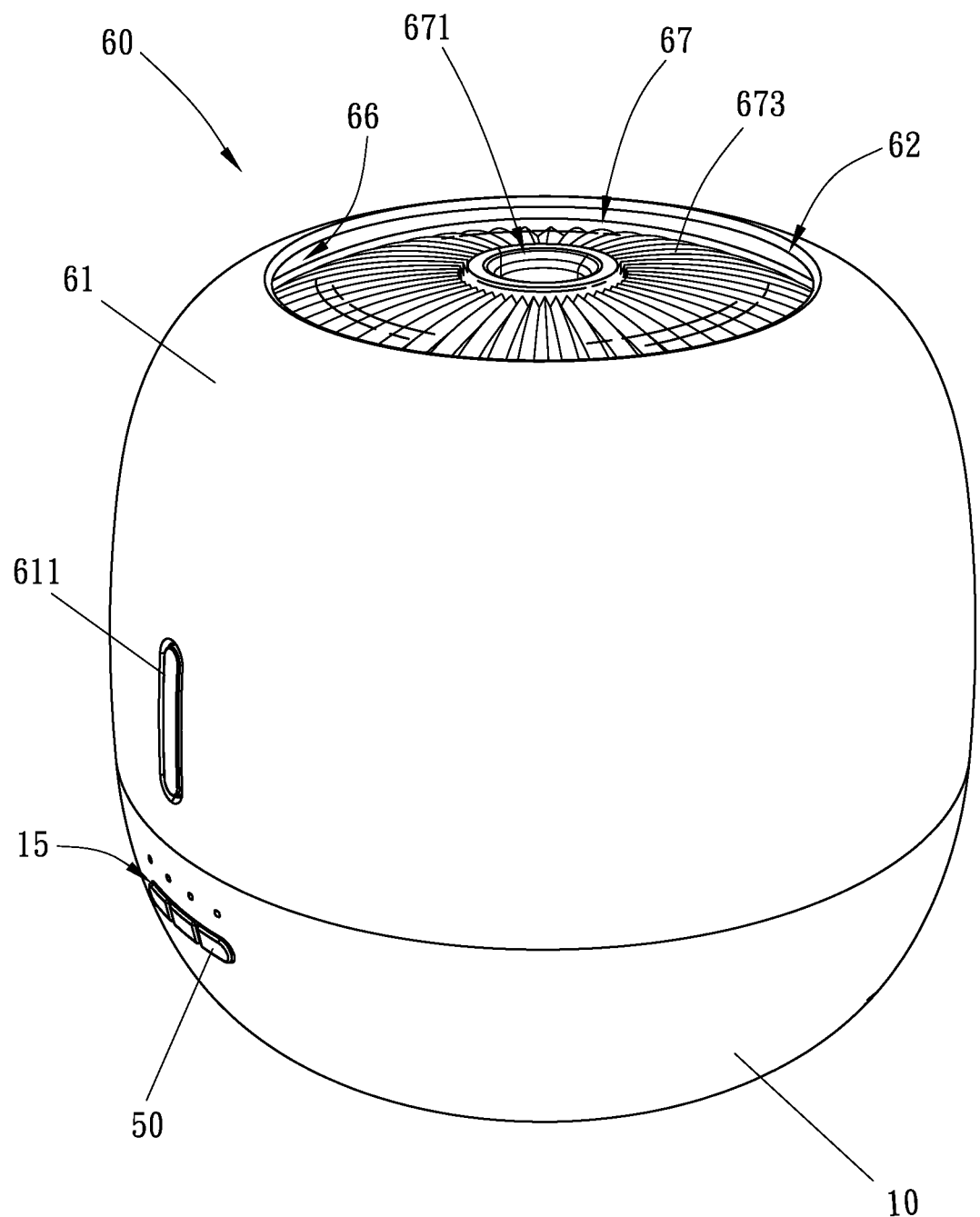
FIG. 1 is an oblique top elevational view of an atomizing diffuser for gaseous environment cleaning in accordance with the present invention.

Referring to FIGS. 1-8, an atomizing diffuser for gaseous environment cleaning in accordance with the present invention is shown. The atomizing diffuser comprises a bottom shell 10, a fan 20, a water tank 30, an oscillation device 40, a housing 60, and a control unit 70.

The bottom shell 10 comprises a chamber 11 internally defined, a first air inlet 12 provided on the bottom side of the chamber 11, and an opening 13 formed on the upper edge of the chamber 11.

The water tank 30 comprises a slot 31, a tank bottom 33, a first hole 34, a tank cover 35, and an air flow channel 37. The slot 31 is formed on the upper side of the water tank 30. The tank bottom 33 opens the first hole 34. One side of the air flow channel 37 protrudes in the water tank 30 to form a protruding pipe vent 371, and the other side of the air flow channel 37 extends out of the tank bottom 33 to form a vent 373. The fan 20 is combined in the vent 373.

The water tank 30 is combined in the opening 13 of the bottom shell 10. The air flow channel 37 and the fan 20 are disposed in communication with the first air inlet 12 through the chamber 11. The first air inlet 12 provides a path for the fan 20 to inhale outside air.

The tank cover 35 comprises an oscillation space 351, a first gap 353, a shield 355, and a first exhaust hole 357. The tank cover 35 is shaped to match the structure of the protruding pipe vent 371 and the first hole 34 in the water tank 30.

The shield 355 forms a recess shape on the inner side of the circumference of the tank cover 35. The inner side of the recess shape of the shield 355 forms a shielded space. The first exhaust hole 357 is formed on the other side of the tank cover 35. The first gap 353 is cut on the bottom side of the tank cover 35. The tank cover 35 is combined with the upper side of the bottom wall 33 inside the water tank 30 to simultaneously cover the first hole 34 and the air flow channel 37, while the shield 355 covers the outside of the protruding pipe vent 371. The tank cover 35 internally defines the oscillation space 351 that contains the liquid, so as to limit the oscillation space 351 inside the smaller tank cover 35. The oscillation space 351 is confined to the small tank cover 35, where the amount of liquid that can be filled is less than the amount of liquid in the water tank 30. Both the protruding pipe vent 371 and the first exhaust hole 357 communicate with the oscillation space 351.

The oscillation device 40 is mounted in the first hole 34, comprising an oscillator 43. The oscillator 43 is externally coated with a layer of acid and alkali resistant coating for vibrating and atomizing the liquid in the oscillation space 351.

The oscillator 43 oscillates and atomizes the less liquid in the oscillation space 351 in the tank cover 35, which can maintain a better atomization effect. At the same time, the water molecules of the atomizing vapor can be concentrated inside the tank cover 35 and effectively outputted through the first exhaust hole 357, while avoiding the dilemma that the oscillation device 40 is not effective in oscillating a large amount of liquid in the large-volume water tank. This can solve the problem that the large-volume storage liquid of the water tank of the existing large-scale diffuser affects the oscillating atomization effect.

The housing 60 comprises a cover shell 61. The cover shell 61 comprises a water filling hole 62 and an inner wall 63. The water filling hole 62 is opened on the upper side of the cover shell 61. The inner wall 63 protrudes downward from the inner side of the cover shell 61 with a surrounding wall structure, and the inner wall 63 corresponds to the lower side of the water filling hole 62.

The housing 60 is detachably assembled to the opening 13 of the bottom shell 10 to shield the tank cover 35. The first exhaust hole 357 of the tank cover 35 corresponds to the inner side of the water filling hole 62, and the free end of the inner wall 63 is connected to the slot 31. The first exhaust hole 357 and the oscillation space 351 are connected to form a spray outlet path.

The control unit 70 is combined in the chamber 11 at one side of the tank bottom 33, comprising a circuit device, such as PCBA, and a driver circuit for driving the oscillation device 40. The control unit 70 is electrically connected to the oscillation device 40, the fan 20, or other lamps, electronics or appliances used in the diffuser, to control the switching or various action functions of the oscillation device 40 or the fan 20 or other lamps, electronics or appliances.

Thereby, the user can pour liquid from the water filling hole 62 into the water tank. The applied liquid flows into the oscillation space 351 from the first gap 353. When a power source is connected to the control unit 70, the control unit 70 turns on the oscillation device 40 to oscillate the liquid in the oscillation space 351 (such as alkaline ionized water or various environmental cleaning and purification preparations, or adding various natural sterilization and deodorants to the applied liquid, thereby producing atomized mist (fine water molecules). At the same time, the fan 20 continues sending the air flow from the first air inlet 12 to the vent 373 to pass through the protruding pipe vent 371 of the air flow channel 37. The airflow is blocked by the shield 355 and flows in the oscillation space 351, and will not directly flow out of the first exhaust hole 357. It can effectively transport the mist (fine water molecules) of the vaporized alkaline ionized water (in the embodiment, the pH value of the hydroxide ionized water electrolyzed with pure water is about 10 to 12.5) from the oscillation space 351 through the first exhaust hole 357 to the external environment space to sterilize, clean, deodorize, eliminate viruses or purify the air in a three-dimensional space in a house or above the ground. It is safe to use does not affect human health.

In one embodiment of the present invention, the oscillation device 40 further comprises an alkaline ionized water or various environmental cleaning and purification preparations or adding various natural sterilization and deodorants to the applied liquid, the alkaline ionized water or various environmental cleaning and purification preparations or adding various natural sterilization and deodorants to the applied liquid L (please refer to the FIG. 8) from the water filling hole 62 into the water tank 30, then flows into the oscillation space 351 from the first gap 353.

In one embodiment of the present invention, the oscillation device 40 comprises a waterproof ring 41, a fixing frame 42, and an oscillator 43. The oscillator 43 is, for example, a ceramic sheet or metal sheet material, such as iron or copper, and the outer layer of the oscillator 43 is coated with the acid and alkali resistant coating to avoid, for example, alkaline ionized water or various environmental cleaning purification agents, or deodorant, disinfectant liquid from corroding the oscillator 43 and causing damage. In one embodiment, the film thickness of the acid and alkali resistant coating is 0.5 to 1.5 microns, or preferably about 1 micron. The acid and alkali resistant coating comprises a fluorine-containing polymer (fluoropolymer) or fluorine-containing oligomers or electronic metal coating agents commonly used in the electronics industry. The oscillation device 40 is set in the first hole 34 at the bottom side of the oscillation space 351. The oscillator 43 is set in the waterproof ring 41, and then the waterproof ring 41 is mounted in the first hole 34. The fixing frame 42 is located at the bottom side of the waterproof ring 41 and fastened to the bottom surface of the tank bottom 33 around the first hole 34 to fix the oscillation device 40 in position. The oscillator 43 is protected by the acid and alkali resistant coating. The diffuser of the present invention can atomize alkaline ionized water or other acid-alkaline liquids without corroding the oscillator 43.

The first waterproof ring 41 can be made of silicon rubber ring, rubber or plastics.

Referring to FIGS. 2 and 3 and FIGS. 6-8, in one embodiment of the present invention, the housing 60 further comprises an umbrella-shaped panel 67. The umbrella-shaped panel 67 is opened with a spray hole 671. The umbrella-shaped panel 67 is combined in the cover shell 61 at an inner side relative to the water filling hole 62. A second gap 66 is maintained between the inner side of the water filling hole 62 and cover shell 61 and the umbrella-shaped panel 67. The housing 60 is detachably assembled to the opening 13 of the bottom shell 10 to shield the tank cover 35. In this way, the user can add supplementary liquid such as alkaline ionized water or various environmental cleaning and purification agents, and conveniently pour the liquid from the water filling hole 62 onto the upper surface of the umbrella-shaped panel 67. The liquid flows into the second gap 66 along the umbrella-shaped panel 67 like rain, while the inner wall 63 guides the liquid to drip into the water tank 30. Then, the liquid flows into the oscillation space 351 in the tank cover 35 through the first gap 353 due to the balance of the water level difference. Since the user does not need to open the housing 60 to add liquid to the water tank, it is convenient to use. The spray hole 671 communicates with the first exhaust hole 357 and the oscillation space 351 to form a spray outlet path. The vaporized alkaline ionized water (in the embodiment, the pH value of the hydroxide ionized water electrolyzed with pure water is about 10 to 12.5) flows from the oscillation space 351 through the first exhaust hole 357 and the spray hole 671 to sterilize, clean, deodorize, eliminate viruses or purify the air in the external environment space.

Referring to FIGS. 2-5, in one embodiment of the present invention, the umbrella-shaped panel 67 thinks about the skeleton structure and visual appearance aesthetics of paper umbrellas from Hakka culture. The umbrella-shaped panel 67 comprises a plurality of radial ribs 673. These radial ribs 673 radiate from the outer edge of the spray hole 671 of the umbrella-shaped panel 67 to the peripheral edge of the umbrella-shaped panel 67. These radial ribs 673, like the ribs of a paper umbrella, have support and decoration functions, which promote the umbrella-shaped panel 67 to have higher rigidity. At the same time, the production of the umbrella-shaped panel 67 can also reduce the material and weight. According to this design, the umbrella-shaped panel 67 can be thinner and lighter in weight. It is decorative and not easy to damage during assembly or when dumping.

In some embodiments of the present invention, the radial ribs 673 are arranged on the inner surface of the umbrella-shaped panel 67 and radially extended from the spray hole 671 to the peripheral edge of the umbrella-shaped panel 67. The material of the umbrella-shaped panel 67 can be selected from a variety of light-permeable translucent or transparent plastic materials, acrylic, glass, etc. The light-permeable translucent or translucent or transparent umbrella-shaped panel 67 vaguely sees through the radial ribs 673. The overall shape is like a paper umbrella, with a decorative effect.

In some embodiments of the present invention, the umbrella-shaped panel 67 is a light-transmitting or transparent material. The radial ribs 673 are formed on the underside of the umbrella-shaped panel 67. The radial ribs 673 radially extend from the outer edge of the spray hole 671 to the peripheral edge of the umbrella-shaped panel 67, and the umbrella-shaped panel 67 can see through the radial ribs 673 on the upper side of the transparent or transparent material.

Figure 5:
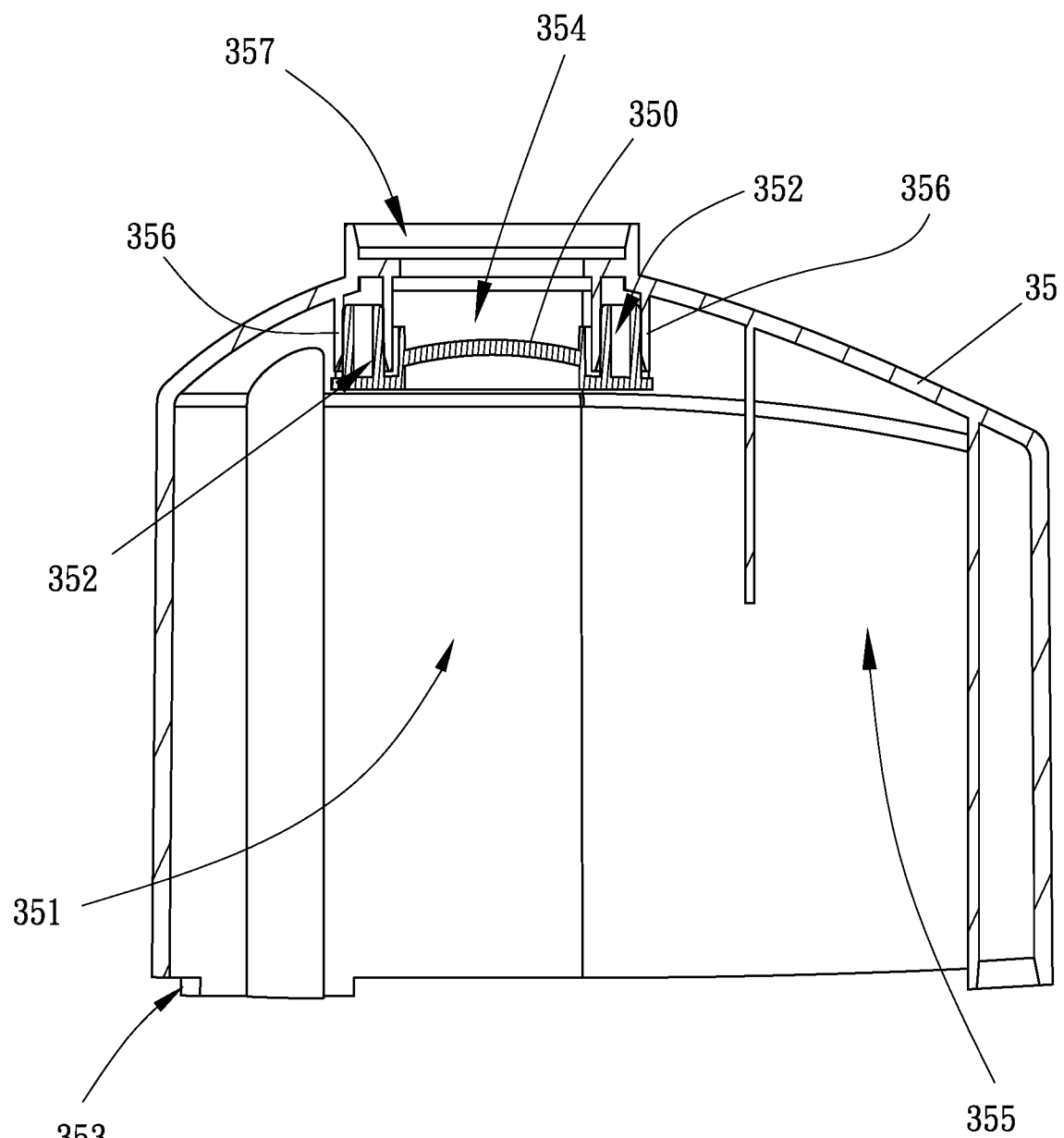
FIG. 5 is a sectional view of the tank cover.
Figure 6:
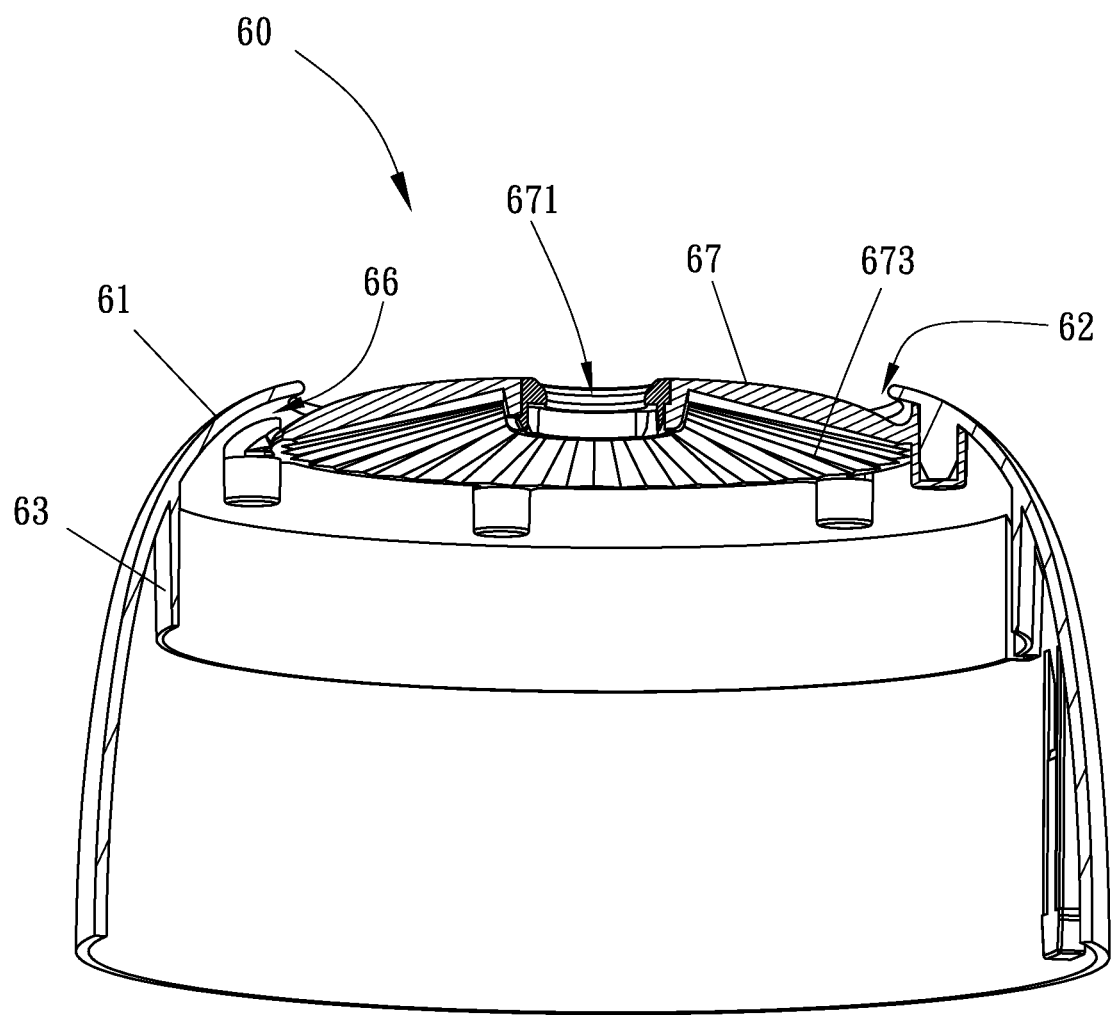
FIG. 6 is a sectional view of the housing.
Figure 7:
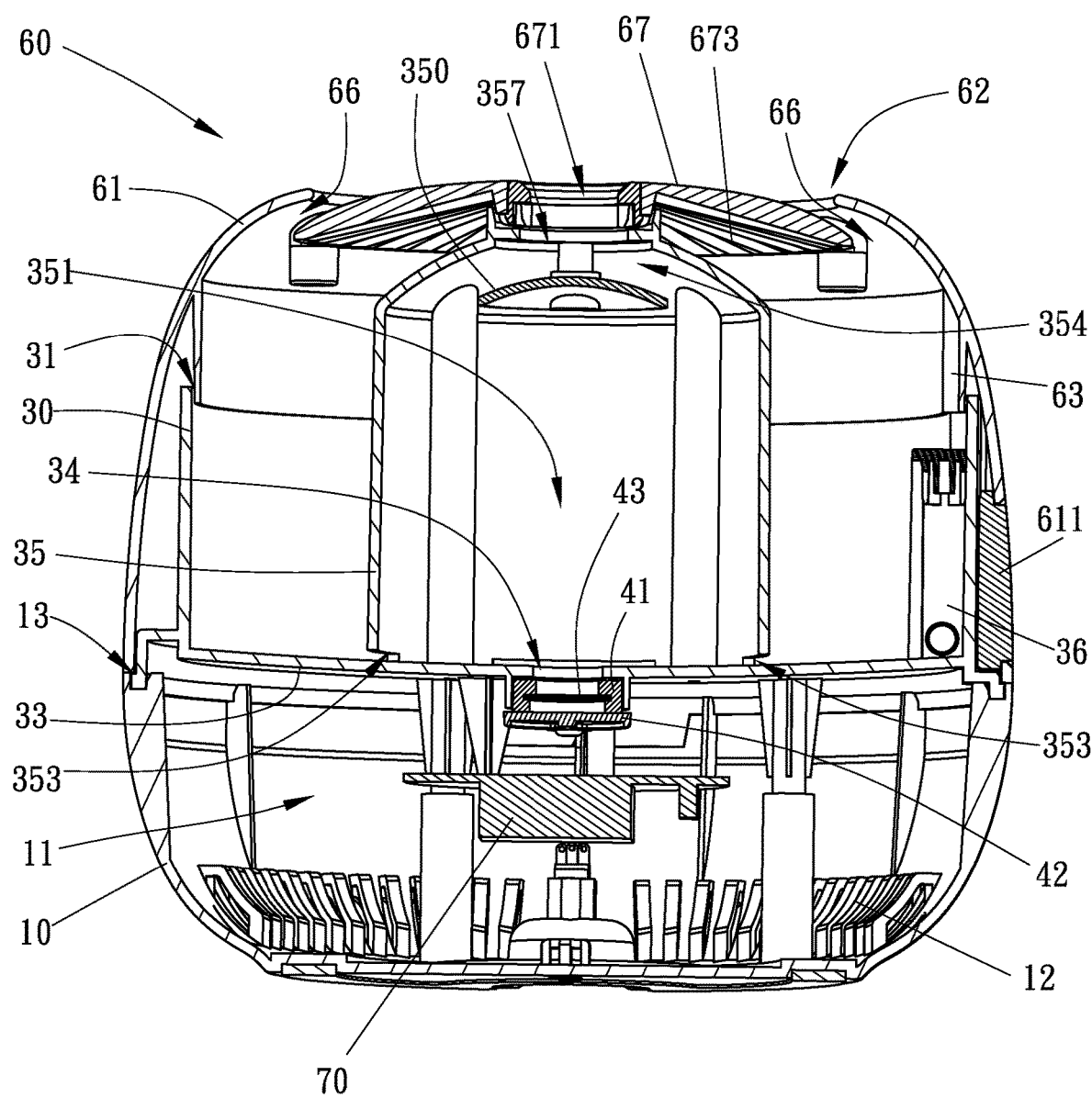
FIG. 7 is a sectional view of the atomizing diffuser for gaseous environment cleaning shown in FIG. 1.
Figure 8:
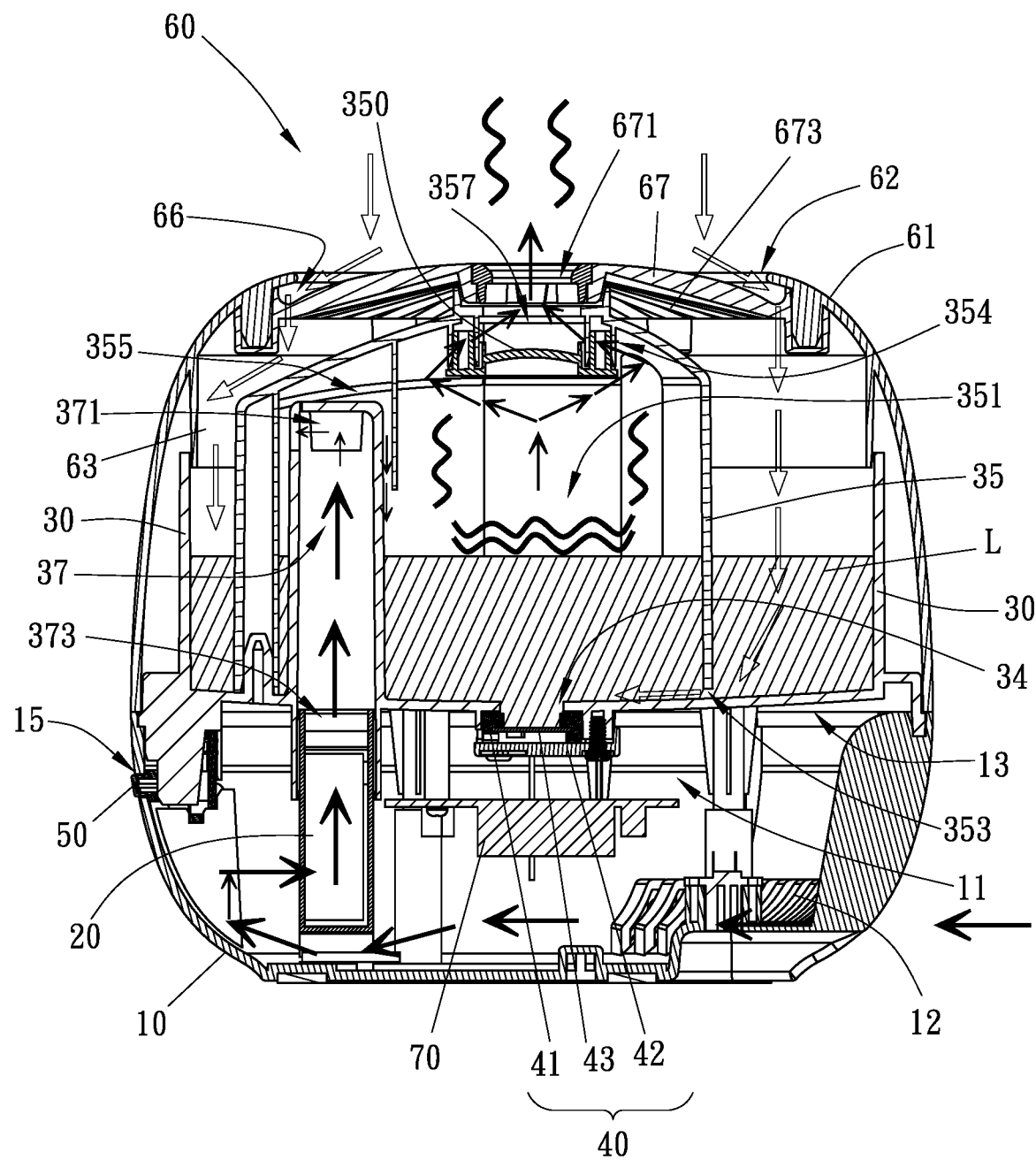
FIG. 8 is a schematic sectional view of the atomizing diffuser of the present invention, showing the air flowing direction.

Referring to FIG. 5, FIG. 7 and FIG. 8, in one embodiment of the present invention, the tank cover 35 further comprises a water baffle 350. The water baffle 350 is combined with the lower side of the first exhaust hole 357. A third gap 354 is maintained between the water baffle 350 and the underside of the first exhaust hole 357. The replenished liquid such as alkaline ionized water is oscillated into a mist in the oscillation space 351, and the mist flows from the third gap 354 through the first exhaust hole 357, and then outputs from the spray hole 671 of the housing 60 to the external space. The oscillating liquid in the oscillation space 351 may not be completely atomized, and the larger water droplets produced are sprayed upward, and the water baffle 350 blocks the water droplets to prevent the water droplets from flowing into the first exhaust port 357 and spray hole 671 to obstruct spray.

Referring to FIG. 5, in one embodiment of the present invention, the water baffle 350 comprises a plurality of engaging portions 352 equiangularly spaced on the upper side thereof. The tank cover 35 has a plurality of retaining grooves 356 located on a bottom surface thereof around the first exhaust hole 357. By means of fastening the engaging portions 352 to the respective retaining groove 356, the water baffle 350 is fastened to the tank cover 35. The joining method is for example a tight fit or a hollow structure on the inside of each engaging portion 352, which has elasticity and tight fit to catch the respective retaining groove 356.

In some embodiment, the control unit 70 further comprises a light source device 71, which comprises, for example, an LED lamp or bulb, and a circuit device. The light source device 71 is electrically connected to the control unit 70. The umbrella-shaped panel 67, the tank cover 35, the shield 355, the water tank 30 and the water baffle 350 can be made of translucent or transparent plastic, acrylic, ceramic or glass, etc. The control unit 70 is electrically connected to an external power source to provide electrical power to the light source device 71, so that the light source device 71 emits light through the translucent or transparent water tank 30 and the tank cover 35 onto the umbrella-shaped panel 67 to provide a light decoration effect. The light falling upon the light-permeable translucent or transparent umbrella-shaped panel 67 is refracted by the radial ribs 673 to produce a light decoration effect that shows the skeleton charm of a paper umbrella. Combining the spray effect of the atomizing diffuser, the automizing diffuser can have a better atmosphere in a gaseous environment. In particular, the water tank 30 can also be additionally added with a fragrance liquid to make the sterilization, disinfection and deodorization smell better.

In some embodiments, the control unit 70 comprises any of various printed circuit board assemblies such as electronic circuits or various computer equipment such as computers or microprocessors, which can be used in the operation or control function of the automizing diffuser of the present invention.

Figure 2:
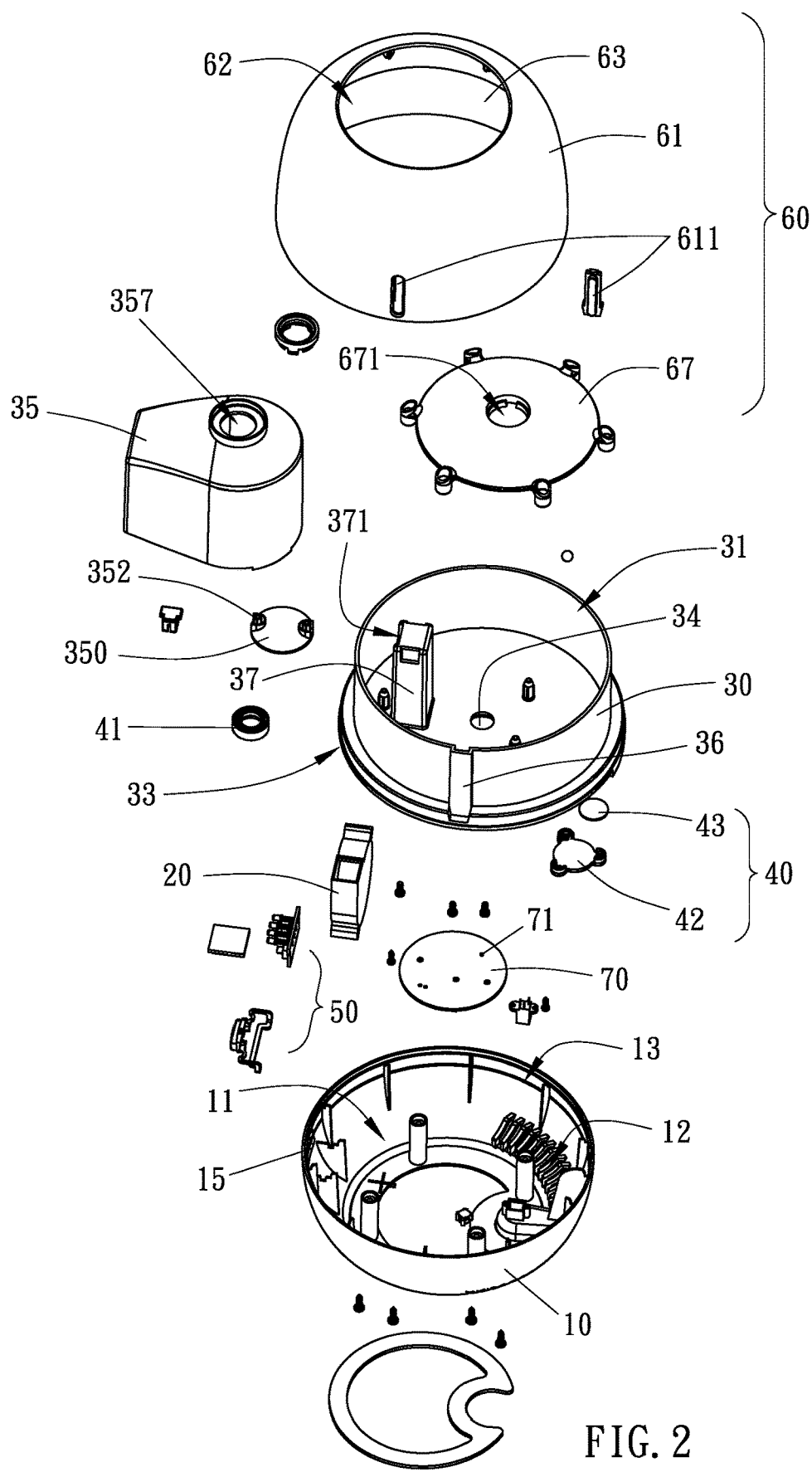
FIG. 2 is an exploded view of the atomizing diffuser for gaseous environment cleaning in accordance with the present invention.
Figure 3:
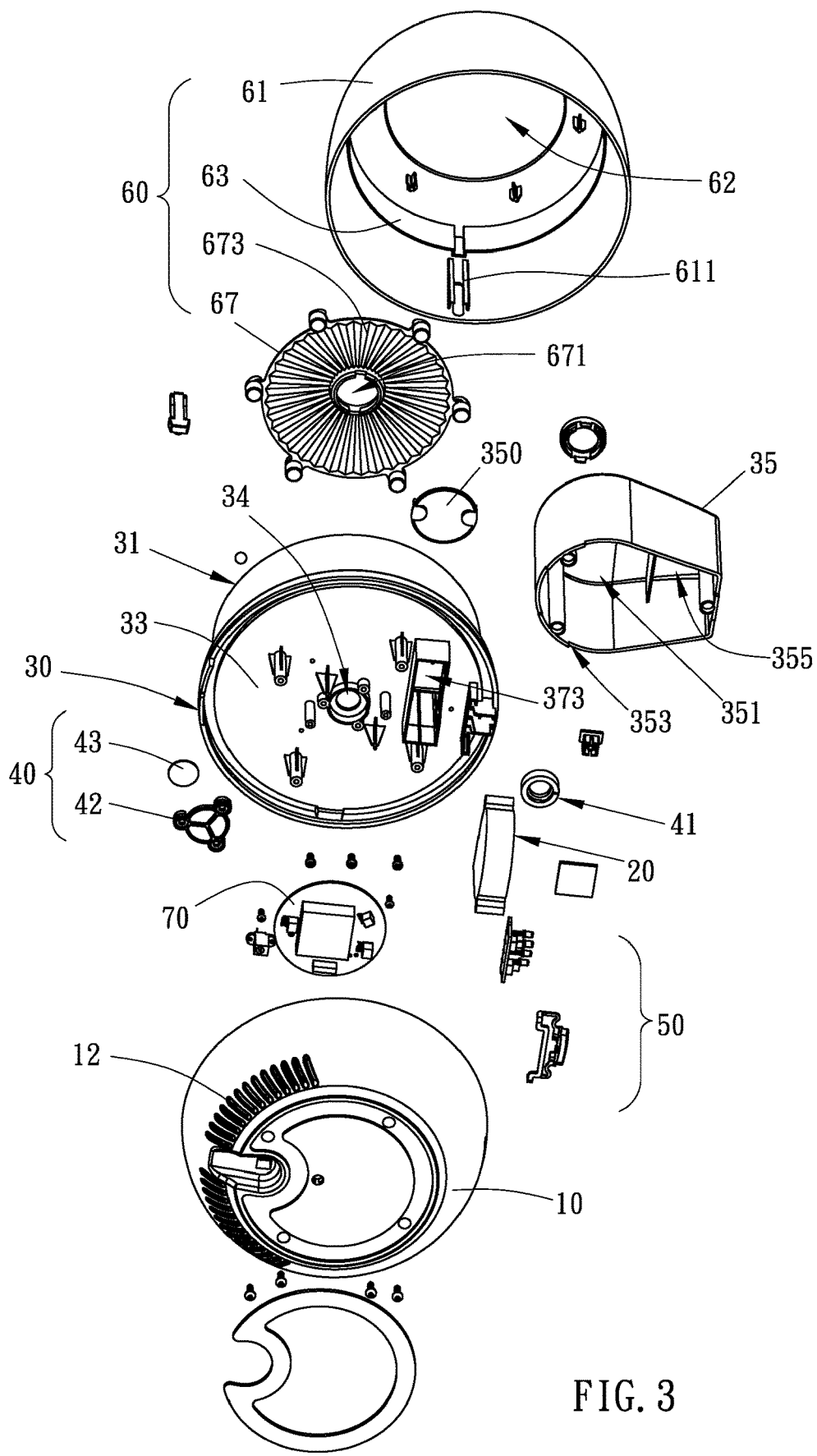
FIG. 3 corresponds to FIG. 2 when viewed from another angle.
Figure 4:
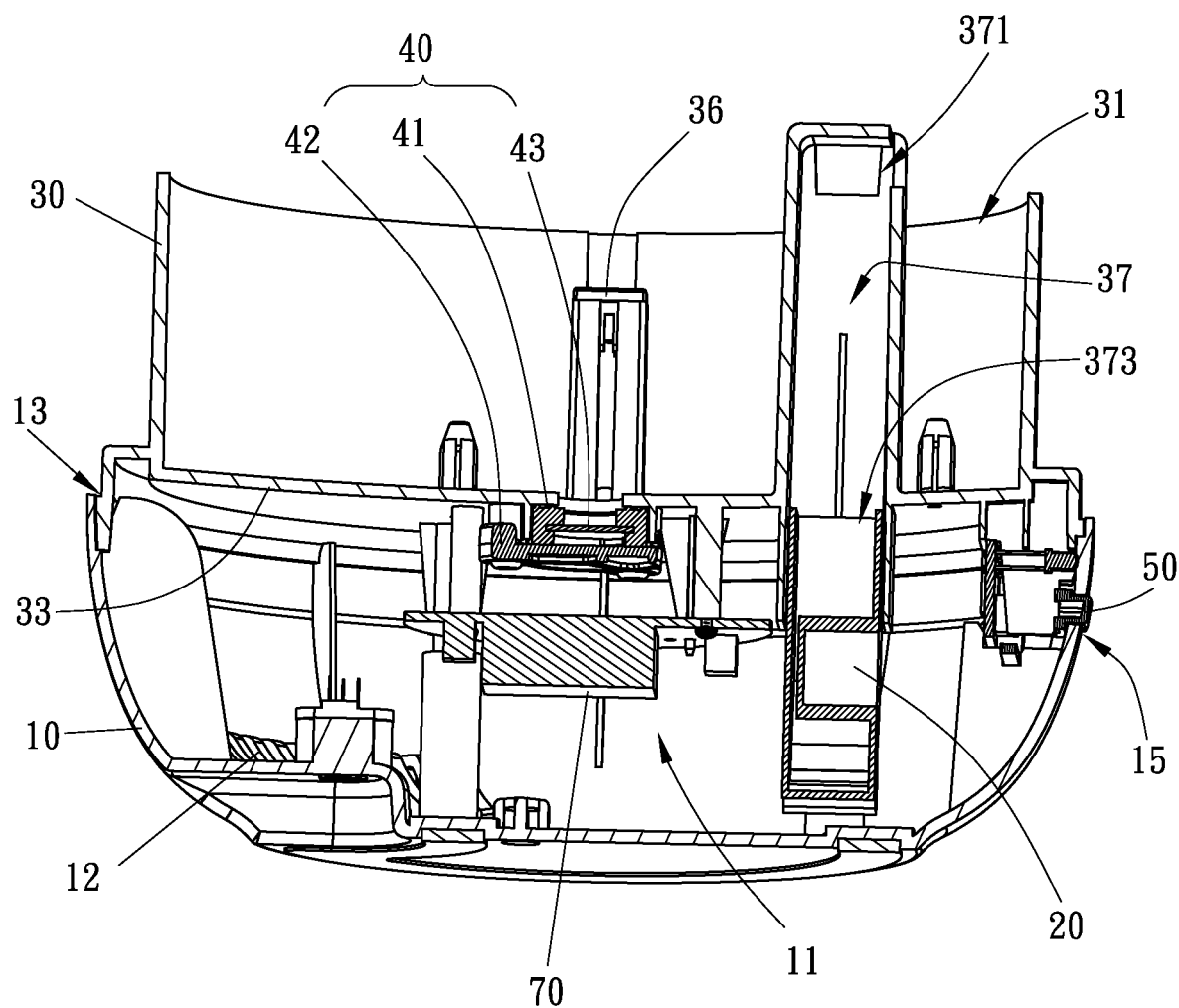
FIG. 4 is a sectional view showing the water tank assembled to the bottom shell.

Referring to FIGS. 2-4, in some embodiments, the diameter of the vent 373 is larger than the protruding pipe vent 371, so that the air flow of the fan 20 flows from the vent 373 to the protruding pipe vent 371, and the pressure air with a higher flow rate can flow to the oscillation space 351. Thus, the generated mist can be quickly and effectively transported by the air flow to the spray hole 671 to escape to the outside of the automizing diffuser.

Referring to FIG. 2, FIG. 4 and FIG. 8, in one embodiment of the present invention, the tank cover 35 is combined with the bottom wall 33 of the water tank 30 to cover the first hole 34 and the air flow channel 37. The shield 355 covers the outside of the protruding pipe vent 371 of the air flow channel 37. The protruding pipe vent 371 forms a height (distance) relative to the inner wall of the tank cover 35. Thereby, the protruding pipe vent 371, which is designed with a tubular protrusion in the water tank 30, has a height (distance) formed relative to the inner wall of the tank cover 35. When the atomizing diffuser is dumped, the liquid in the oscillation space 351 in the tank cover 35 of the water tank 30 can avoid the part of the protruding pipe vent 371 under the influence of gravity, and can be poured on the inner wall of the water tank 30 and the tank cover 35. Therefore, the inclined liquid is less likely to flow directly into the protruding pipe vent 3711, and the liquid is not easy to enter the inside of the atomizing diffuser, which helps to avoid damage to the electronic parts and electrical contacts of the control unit 70 and the fan 20.

Referring to FIG. 2, FIG. 4 and FIG. 8, in one embodiment of the present invention, the vent opening direction of the protruding pipe vent 371 is perpendicular to the inner side wall of the tank cover 35 and at the same time facing the inner side wall of the tank cover 35 (the protruding tube vent 371 is a horizontal opening). Thereby, when the atomizing diffuser is dumped, the liquid gravity flow direction (downward) in the tank cover 35 that leans into the vent opening direction of the protruding pipe vent 371 is opposite to the vent opening direction of the protruding pipe vent 371. The liquid is not easy to flow upwards into the protruding pipe vent 371 under the influence of gravity, and the liquid in the water tank 30 and the tank cover 35 is more difficult to enter the atomizing diffuser.

Referring to FIG. 1, FIG. 4 and FIG. 8, in one embodiment of the present invention, the atomizing diffuser further comprises a switch device 50. The switch device 50 comprises a power switch button, and the switch device 50 is electrically connected to the control unit 70. The bottom shell 10 is provided with a side hole 15. The switch device 50 is mounted in the side hole 15.

Referring to FIGS. 1-3 and FIG. 7, in some embodiments of the present invention, the water tank 30 has a transparent suspension trough 36 formed on one side. The transparent suspension trough 36 has a floating ball put therein. The cover shell 61 has a view window 611 on one side thereof. The transparent suspension trough 36 is combined with the view window 611. The water level in the transparent suspension trough 36 is observed through the view window 611.

In one embodiment of the present invention, the atomizing diffuser uses a cleaning, sterilizing, disinfecting and/or deodorizing liquid. For example, select alkaline ionized water with a pH value of 10.0 or more, such as electrolysis of alkaline ionized water with a pH value of 10.5, 11, 11.5, 12, and 12.5. In the preferred embodiment, for example, the pH value of the hydroxide ionized water of pure water electrolysis is 10 to 12.5, and the alkaline ionized water has a peeling effect, can neutralize static electricity, and float away from dirt; alkalization can decompose oil or protein and has stronger permeability than general water, with good cleaning and sterilization effects.

In one embodiment, the electrolyzed hydroxide ion water with a pH value of 12.5 is filled into the water tank 30 and the oscillation space 351 of the tank cover 35. The user turns on the power of the switch device 50 to the control unit 70 to instruct the fan 20 and the oscillation device 40 to operate, and the oscillation device 40 generates vibration, causing the alkaline ionized water in the oscillation space 351 to generate mist. At the same time, the fan 20 sucks in the outside air through the first air inlet 12 of the bottom shell 10. The suction air passes through the air flow channel 37 to the shield 355 and flows into the oscillation space 351. The generated mist of alkaline ionized water is carried by the air flow to pass from the oscillation space 351 through the third gap 354, the first exhaust hole 357 and the spray hole 671 to the environment space outside the atomizing diffuser to sterilize, clean, deodorize, eliminate viruses or purify the air. The atomizing diffuser is safe to use and does not affect human health.

Although particular embodiments of the present invention have been described in detail for purposes of illustration, various modifications and enhancements may be made without departing from the spirit and scope of the invention. Accordingly, the invention is not to be limited except as by the appended claims.

What the invention claimed is:

1. An atomizing diffuser for gaseous environment cleaning, comprising a bottom shell, a fan, a water tank, an oscillation device, a housing, and a control unit;
   wherein:
   said bottom shell comprises a chamber defined therein, a first air inlet located in a bottom side of said chamber, and an opening formed on an upper edge of said chamber;

said water tank comprises a slot, a tank bottom, a first hole, a tank cover and an air flow channel, said slot being formed on an upper side of said water tank, said tank bottom opening said first hole, said air flow channel having one side thereof protruding in said water tank to form a protruding pipe vent and an opposite side thereof extending out of said tank bottom to form a vent, said vent accommodating said fan, said water tank being combined in said opening of said bottom shell, said air flow channel and said fan being communicated with said first air inlet in said chamber;

said tank cover comprises an oscillation space, a first gap, a shield and a first exhaust hole, said shield forming a recess shape on an inner side of the circumference of said tank cover, said recess shape of said shield having an inner side forming a shielded space, said first exhaust hole being formed on an opposite side of said tank cover, said first gap being cut on a bottom side of said tank cover, said tank cover being combined with an upper side of a bottom wall inside said water tank to simultaneously cover said first hole and said air flow channel, said shield covering said protruding pipe vent, said tank cover internally defining said oscillation space, said protruding pipe vent and said first exhaust hole communicating with said oscillation space;

said oscillation device is mounted in said first hole, said oscillation device comprising an oscillator, said oscillator being externally coated with a layer of acid and alkali resistant coating;

said housing comprises a cover shell, said cover shell comprising a water filling hole and an inner wall, said water filling hole being opened on an upper side of said cover shell, said inner wall protruding downward from an inner side of said cover shell with a surrounding wall structure, said inner wall corresponding to a lower side of said water filling hole, said housing being detachably assembled to said opening of said bottom shell to shield said tank cover, said first exhaust hole of said tank cover corresponding to an inner side of said water filling hole, said inner wall having a free end thereof connected to said slot, said first exhaust hole and said oscillation space being connected to form a spray outlet path;

said control unit is combined in said chamber at one side of said tank bottom and electrically connected with said oscillation device and said fan.

2. The atomizing diffuser for gaseous environment cleaning as claimed in claim 1, wherein said acid and alkali resistant coating comprises a fluorine-containing polymer (fluoropolymer) or fluorine-containing oligomers or electronic metal coating agent.

3. The atomizing diffuser for gaseous environment cleaning as claimed in claim 1, wherein the film thickness of the acid and alkali resistant coating is 0.5 to 1.5 microns.

4. The atomizing diffuser for gaseous environment cleaning as claimed in claim 3, wherein the film thickness of the acid and alkali resistant coating is 1 micron.

5. The atomizing diffuser for gaseous environment cleaning as claimed in claim 1, wherein said housing further comprises an umbrella-shaped panel, said umbrella-shaped panel being opened with a spray hole, said umbrella-shaped panel combined in said cover shell at an inner side relative to said water filling hole so that a second gap is maintained between an inner side of said water filling hole and said cover shell and said umbrella-shaped panel, said spray hole being communicated with said first exhaust hole and said oscillation space.

6. The atomizing diffuser for gaseous environment cleaning as claimed in claim 5, wherein said umbrella-shaped panel comprises a plurality of radial ribs radially extended from said spray hole to the peripheral edge of said umbrella-shaped panel.

7. The atomizing diffuser for gaseous environment cleaning as claimed in claim 6, wherein said umbrella-shaped panel is selectively made of a light-permeable translucent or transparent material; said radial ribs are formed on a bottom side of said umbrella-shaped panel and radially extended from said spray hole to the peripheral edge of said umbrella-shaped panel.

8. The atomizing diffuser for gaseous environment cleaning as claimed in claim 5, wherein said tank cover further comprises a water baffle, said water baffle being combined with a lower side of said first exhaust hole so that a third gap is maintained between said water baffle and the lower side of said first exhaust hole.

9. The atomizing diffuser for gaseous environment cleaning as claimed in claim 8, wherein said water baffle comprises a plurality of engaging portions equiangularly spaced on an upper side thereof; said tank cover comprises a plurality of retaining grooves located on a bottom surface thereof around said first exhaust hole for the engagement of the respective said engaging portions of said water baffle.

10. The atomizing diffuser for gaseous environment cleaning as claimed in claim 8, wherein said control unit further comprises a light source device, said control unit being electrically connected to an external power source to provide electrical power to said light source device for causing said light source device to emit light toward said umbrella-shaped panel, said tank cover, said shield, said water tank and said water baffle; said umbrella-shaped panel, said tank cover, said shield, said water tank and said water baffle are selectively made of a light-permeable translucent or transparent material.

11. The atomizing diffuser for gaseous environment cleaning as claimed in claim 1, wherein said shield covers outside of said protruding pipe vent of said air flow channel, and said protruding pipe vent forms a height (distance) relative to an inner wall of said tank cover.

12. The atomizing diffuser for gaseous environment cleaning as claimed in claim 11, wherein vent opening direction of said protruding pipe vent is perpendicular to an inner side wall of said tank cover and at the same time facing the inner side wall of said tank cover.

13. The atomizing diffuser for gaseous environment cleaning as claimed in claim 1, wherein the atomizing diffuser further comprises a switch device, the switch device comprises a power switch button, and the switch device is electrically connected to the control unit, the bottom shell is provided with a side hole, the switch device is mounted in the side hole.

14. The atomizing diffuser for gaseous environment cleaning as claimed in claim 1, wherein the water tank has a transparent suspension trough formed on one side, the transparent suspension trough has a floating ball put therein, the cover shell has a view window on one side thereof, the transparent suspension trough is combined with the view window the water level in the transparent suspension trough is observed through the view window.

15. The atomizing diffuser for gaseous environment cleaning as claimed in claim 1, wherein further comprises an alkaline ionized water or various environmental cleaning and purification preparations or adding various natural sterilization and deodorants to the applied liquid, the alkaline ionized water or various environmental cleaning and purification preparations or adding various natural sterilization and deodorants to the applied liquid from the water filling hole into the water tank, then flows into the oscillation space from the first gap.

16. The atomizing diffuser for gaseous environment cleaning as claimed in claim 15, wherein the alkaline ionized water is hydroxide ionized water.

* * * * *